(12) United States Patent
Thoorens et al.

(10) Patent No.: US 8,632,818 B2
(45) Date of Patent: Jan. 21, 2014

(54) MICROCRYSTALLINE CELLULOSE AND CALCIUM PHOSPHATE COMPOSITIONS USEFUL AS PHARMACEUTICAL EXCIPIENTS

(75) Inventors: Gregory Thoorens, Ganshoren (BE); Bruno LeClercq, Brussels (BE); Thomas Ruszkay, Hockessin (DE)

(73) Assignee: FMC Corporation, Philadelphia, PA (US)

( * ) Notice: Subject to any disclaimer, the term of this patent is extended or adjusted under 35 U.S.C. 154(b) by 49 days.

(21) Appl. No.: 12/917,991

(22) Filed: Nov. 2, 2010

(65) Prior Publication Data

US 2011/0104271 A1    May 5, 2011

Related U.S. Application Data

(60) Provisional application No. 61/258,390, filed on Nov. 5, 2009.

(51) Int. Cl.
*A61K 9/16* (2006.01)
*A61K 9/20* (2006.01)
*A61K 47/38* (2006.01)
*G01N 3/08* (2006.01)

(52) U.S. Cl.
USPC ........... 424/499; 424/400; 424/465; 424/602; 424/682; 241/27

(58) Field of Classification Search
None
See application file for complete search history.

(56) References Cited

U.S. PATENT DOCUMENTS

| | | | |
|---|---|---|---|
| 4,744,987 A | 5/1988 | Mehra | |
| 5,747,067 A | 5/1998 | Auguello | |
| 5,858,409 A | 1/1999 | Karenty | |
| 6,866,867 B2 | 3/2005 | Staniforth | |
| 6,936,277 B2 | 8/2005 | Staniforth et al. | |
| 6,936,628 B2 | 8/2005 | Lee | |
| 2003/0206978 A1 | 11/2003 | Sherwood et al. | |
| 2005/0075335 A1* | 4/2005 | Buxton et al. | 514/229.8 |
| 2005/0147673 A1 | 7/2005 | Staniforth et al. | |
| 2008/0213360 A1 | 9/2008 | Thoorens et al. | |

FOREIGN PATENT DOCUMENTS

| | | |
|---|---|---|
| EP | 1226818 | 7/2002 |
| WO | WO 8102521 A1 | 9/1981 |
| WO | WO 94-24888 A1 | 11/1994 |
| WO | WO 03/096963 A1 | 11/2003 |
| WO | WO 2005/030116 A1 | 4/2005 |
| WO | WO 2005/030379 A1 | 4/2005 |
| WO | WO 2005/030115 A1 | 3/2006 |
| WO | WO 2006/032828 A1 | 3/2006 |

OTHER PUBLICATIONS

Freitag, et al., "Coprocessing of Powdered Cellulose and Magnesium Carbonate: Direct Tableting Versus Tableting After Roll Compaction/Dry Granulation". Pharmaceutical Development and Technology, 10, pp. 353-362, (2005).
Kleinebudde P., "Roll Compaction/Dry Granulation: Pharmacuetical Applications", European Journal of Pharmaceutics and Biopharmaceutics 58, pp. 317-326, (2004).
Rowe, et al., "Handbook of Pharmaceutical Excipients, Sixth Edition, Milled Material (Anahydrous Dibasic Calcium Phosphate) is Typically use in Wet-granulated or Roller-compacted Formulations", (2009).
Budenheim, Di-Cafos PA, Used as "Dry and Wet Granulation Fillers" 3 pages, (May 2010).
Notification of Transmittal of the International Search Report and the Written Opinion of the International Searching Authority, or the Declaration, International Application No. PCT/U52010/055102, mailing date of Jul. 29, 2011.

\* cited by examiner

*Primary Examiner* — Frederick Krass
*Assistant Examiner* — Michael P Cohen
(74) *Attorney, Agent, or Firm* — FMC Corporation (57) ABSTRACT

Compositions containing calcium phosphate and microcrystalline cellulose are useful as excipients in the preparation of solid dosage forms containing active pharmaceutical ingredients, particularly those prepared by processes involving multiple compaction steps. The recompactibility performance of such compositions is improved through the use of calcium phosphate having a relatively small particle size, e.g., a median particle size of not more than about 20 microns or not more than about 10 microns.

15 Claims, 7 Drawing Sheets

MICROCRYSTALLINE CELLULOSE AND CALCIUM PHOSPHATE COMPOSITIONS USEFUL AS PHARMACEUTICAL EXCIPIENTS

FIELD OF THE INVENTION

This invention relates to particulate compositions useful as excipients in pharmaceutical formulations and granulates and solid dosage forms containing such excipients and active pharmaceutical ingredients.

DESCRIPTION OF THE RELATED ART

Discrete dosages of pharmaceutical compositions suitable for oral administration are conveniently administered as solid dosage forms, typically tablets. In addition to the therapeutic ingredient or ingredients (commonly referred to as "actives," "active pharmaceutical ingredients," or "APIs"), the tablet comprises pharmaceutically acceptable materials, known as excipients, that are not actives and do not provide a therapeutic effect, but are added to the tablet formulation to confer specific properties not related to the activity of the active.

There are three general methods of preparation of tablets: (1) direct compression; (2) dry granulation; and (3) wet granulation. In direct compression, the powdered material(s) to be included in the tablet (including the active and the excipients) are blended together and compressed directly without intermediate processing, such as granulation. Although direct compression is the most effective and favorable manufacturing process for the production of solid dosage forms, such as tablets, many tablet formulations cannot be processed using direct compression due to certain properties of the formulations such as poor flow or low bulk density. For example, poor flow properties may result in unacceptably high variances in drug dosages from tablet to tablet.

Granulation procedures may be used where poor flow or low bulk density of the direct compression mix precludes tableting by direct compression. Granulation also improves content uniformity of the active, and reduces dust generation. Dry granulation includes mixing the ingredients (which may include the active as well as one or more excipients such as binders, fillers, disintegrants, or lubricants), roller compacting or slugging the mix, dry screening or milling to a coarse dry granulate and compressing the granules. The granules may be combined with one or more further excipients (binder, distintegrant, lubricant, etc.) prior to recompaction. The wet granulation procedure includes mixing some or all of the ingredients and thereafter adding water to the mixed powders (alternatively, one or more of the ingredients, particularly a binder, may be in suspension or solution when combined with the other ingredients). The resulting wet mass is screened, dried, optionally combined with one or more further excipients such as lubricant, binder, filler or disintegrant, and compressed into tablets.

In dry granulation, the tablet ingredients are not exposed to moisture, solvents and heat. Thus, dry granulation can be used to process moisture, solvent and/or heat sensitive actives. Dry granulation can be carried out by slugging or by roller compaction. Slugging is a double compression process. The material to be tableted is compressed to a large compressed mass, or "slug," which is milled to a granulate, with the granulate then converted to tablets by a second compression process. Because slugging is a slow and uneconomic process, roller compaction has become the method of choice for dry granulation. Roller compaction has all the benefits of a granulation process, such as improved material flow behavior and content uniformity. In addition, roller compaction is high-volume and more economical to operate than wet granulation.

During the roller compaction process, at least a portion of the tablet formulation (the "granulate formulation") is compacted and densified by two counter-rotating high-pressure rollers, and the resulting material milled to uniform size. The resulting granulate may be subsequently tableted with or without additional excipients to form tablets. The tablet is formed by pressure acting on the tablet formulation in a die on a tablet press. A tablet press includes a lower punch which fits into a die from the bottom and an upper punch having a corresponding shape and dimension, which enters the die cavity from the top after the tablet formulation fills the die cavity. The tablet is formed by pressure applied to the tablet formulation in the die by the lower and upper punches.

Because of its inherent compactibility characteristics, microcrystalline cellulose (MCC) finds widespread use as an excipient in pharmaceutical formulations. Good binding and disintegration properties are also obtained when MCC is used in tablet formulations.

Tablet formation by roller compaction followed by tableting includes two compaction steps. However, after the first compaction step, the granulate may have insufficient compactibility for the second compaction, i.e., tableting, step. Therefore a need exists for improved binders that can be used to prepare solid dosage forms by processes involving multiple compaction steps such as roller compaction and tableting, or slugging. The binder must have sufficient compactibility for the second compaction step. Unfortunately, adequate recompactibility has proven to be challenging to achieve without comprising certain other desirable properties. For example, certain binders that exhibit satisfactory recompactibility may have poor flow characteristics. Other binders may be sensitive to the presence of lubricant in the formulation. That is, recompactibility performance may be adequate in the absence of lubricant or at low lubricant concentrations, but unsatisfactory when the amount of lubricant is increased to the level necessary to facilitate tablet ejection from the die following compaction. Additionally, in some cases, a binder displays acceptable recompactibility at low tableting pressures, but poorer recompactibility at higher tableting pressures (such that the tablets start to cap or laminate, resulting in tablet defects). It would be desirable to develop binders possessing good recompactibility across a wide range of tableting pressures, thereby enhancing their versatility.

BRIEF SUMMARY OF THE INVENTION

The invention provides a composition useful as a pharmaceutical excipient comprising a physical blend of particles of at least one calcium phosphate and particles of microcrystalline cellulose, wherein the particles of at least one calcium phosphate have an median (D50) particle size as measured by laser diffraction of not greater than about 20 microns (the composition hereinafter sometimes being referred to as "the particulate product of the invention"). The term "physical blend" as used in this specification refers to a blend obtained by dry blending (mixing) of the calcium phosphate particles and microcrystalline cellulose particles.

In accordance with the present invention, a composition of matter useful as a pharmaceutical excipient is provided which includes a physical blend of particulate microcrystalline cellulose and particulate calcium phosphate, the two components in one embodiment being present in a weight ratio of from about 85:15 to about 55:45 microcrystalline cellulose:

calcium phosphate and the calcium phosphate having an median particle size not greater than about 20 microns.

Microcrystalline cellulose and dibasic calcium phosphate have commonly been used as individual ingredients in the form of physical dry blends in dry granulation processes (i.e., slugging or roller compaction). However, it has now been unexpectedly discovered that the recompactibility performance of a particulate product produced by physically blending calcium phosphate particles and microcrystalline cellulose particles may be significantly improved by controlling the particle size of the calcium phosphate. In particular, when the median calcium phosphate particle size is selected to be not more than about 20 microns or, more preferably, not more than about 10 microns, granules prepared by compacting a granulate formulation containing such a particulate product as an excipient exhibit higher tensile strengths at a given recompaction pressure than analogous granules prepared using larger particle size calcium phosphate. Alternatively, to achieve a desired tensile strength in a ribbon or tablet, a lower compaction pressure is needed when the particulate product of the invention is used in place of an analogous dry physical blend of microcrystalline cellulose and larger particle size calcium phosphate. The enhanced functionality of the particulate product of the invention provides strong roller-compacted ribbons or slugs, which enables satisfactory roller compaction of otherwise poorly compactible active pharmaceutical ingredients. The need to use extragranular excipients is reduced or avoided altogether due to the improved recompaction characteristics of the particulate product furnished by the present invention.

Thus, in one embodiment of the invention, granules are prepared by roller compacting a dry mixture comprising the particulate product of the invention and at least one active pharmaceutical ingredient (API), optionally also comprising at least one disintegrant and/or at least one lubricant and/or at least one filler, and grinding (milling) the resulting compacted ribbon to produce granules. The granules are then compacted to form tablets or other solid dosage forms. Alternatively, the granules may also be used as such (without being recompacted) in sachets or hard capsules, for example.

In yet another aspect, a granulate or tablet formulation is provided which comprises at least one active (i.e., an API) and a particulate product obtained by a process comprising dry blending of microcrystalline cellulose particles and calcium phosphate particles, wherein the calcium phosphate particles have an median particle size of not greater than about 20 microns, more preferably not greater than about 15 microns, or most preferably not greater than about 10 microns.

Still another aspect of the invention provides a method for making a granulate, wherein the method comprises the steps of:
 a) applying pressure to a granulate formulation to form a compact; and
 b) milling the compact to form a granulate;
wherein the granulate formulation comprises at least one active (i.e., an API) and a particulate product obtained by a process comprising dry blending of microcrystalline cellulose particles and calcium phosphate particles, wherein the calcium phosphate particles have an median particle size of not greater than about 20 microns, more preferably not greater than about 15 microns, or most preferably not greater than about 10 microns.

The granulate thus obtained may be recompacted to provide a solid dosage form such as a tablet.

Further provided by the invention is a solid dosage form comprising a particulate product, at least one active, and, optionally, at least one additional excipient (e.g., a filler, binder, lubricant, disintegrant, and/or glidant) in the form of a compacted tablet, wherein the particulate product is obtained by a process comprising dry blending of microcrystalline cellulose particles and calcium phosphate particles, wherein the calcium phosphate particles have an median particle size of not greater than about 20 microns, more preferably not greater than about 15 microns, or most preferably not greater than about 10 microns.

The particulate product of the invention can provide one or more of the following benefits or advantages when utilized as a pharmaceutical excipient. The need to use multiple different excipients or to introduce portions of the same excipient at different points in a granulation/tableting process may be reduced or eliminated altogether, thereby simplifying such processes, lowering manufacturing costs, and/or improving quality control. A compacted material prepared using the particulate product of the invention can exhibit a decreased tendency to generate fines when milled and screened into a granulate; this can minimize waste and/or avoid the need to recycle particles that are too small to be utilized in a subsequent tableting step. Similarly, tablets containing the particulate product of the invention can have reduced friability as compared to tablets prepared using other binders (e.g., physical blends of microcrystalline cellulose and calcium phosphate particles). The tablets thus can display enhanced resistance to physical handling, helping to ensure that such tablets are intact and undamaged when they reach the consumer. Also, since a tableting formulation containing the particulate product of the invention can use a lower compaction pressure to achieve a desired tensile strength, less wear on the tableting equipment can be realized. In addition, improved yields can be obtained, as fewer tablets will fail to meet the minimum tensile strength requirements.

DESCRIPTION OF THE DRAWINGS

All the figures are described in more detail in the Examples section.

DETAILED DESCRIPTION OF CERTAIN EMBODIMENTS OF THE INVENTION

The particulate product of this invention contains two essential components, microcrystalline cellulose and calcium phosphate. The two components are preferably present in the product in a weight ratio in the range of about 90:10 to about 50:50, or about 85:15 to about 55:45, or about 80:20 to about 60:40 microcrystalline cellulose:calcium phosphate, although other ratios may also provide satisfactory performance depending upon the particular choice of components, particle size, and so forth.

In one aspect of the invention, microcrystalline cellulose and calcium phosphate are the only constituents of the particulate product. However, one or more other ingredients may also be incorporated into the particulate product during its preparation. These are ordinarily present in relatively small amounts, representing less than 30%, and preferably less than 20%, of the total particulate product weight. Such additives may be incorporated to provide enhanced properties for the particulate product in its use as a pharmaceutical excipient. Examples of additives in these categories are binders, e.g., water-soluble gums like hydroxypropylmethylcellulose, methylcellulose, polyvinylpyrrolidone, etc.; lubricants, e.g., long chain fatty acid esters or salts thereof like palmitic and stearic acids; and disintegrants like cross-linked carboxymethylcellulose, starch, etc.

The particulate product of this invention possesses desirable performance attributes that are not shown with corresponding physical blends of microcrystalline cellulose particles and larger size calcium phosphate particles (i.e., calcium phosphate having an median particle size greater than 20 microns, such as direct compression grades of calcium phosphate).

Generally speaking, it will be desirable for the median particle size of the microcrystalline cellulose to be greater than the median particle size of the calcium phosphate. For example, in certain embodiments the median particle size of the microcrystalline cellulose will be at least two, three, four or five times greater than the median particle size of the calcium phosphate.

The combination of microcrystalline cellulose and calcium phosphate is obtained by dry blending these two ingredients in a blender, a tumbler or mixer, with or without the presence of an intensifier bar. Depending on the particle size and the cohesive nature of these excipients, it might be preferred to sieve a pre-blend before introducing these ingredients in the final blender.

Microcrystalline cellulose and calcium phosphate might also be blended together with fillers (such as lactose), with disintegrants (such as croscarmellose sodium), with binders (such as polyvinylpyrrolidone), with matrix formers (such as carrageenan, alginate, or hydroxypropylmethylcellulose), or even with active pharmaceutical ingredients. Lubricants are preferably added to the aforementioned blend in a second blend step, to maintain lubrication time to a minimum to avoid overlubricating the whole formulation. In one embodiment of the invention, the microcrystalline cellulose and calcium phosphate are first mixed to form a pre-blend, with the pre-blend then being combined and mixed with one or more additional components to provide a granulate or tablet formulation (i.e., a composition suitable for processing into granules or a solid dosage form such as a tablet. In another embodiment, the microcrystalline cellulose and calcium phosphate are combined with one or more additional components before being mixed. For example, to provide a granulate or tablet formulation containing microcrystalline cellulose, calcium phosphate, an active, and a lubricant, the microcrystalline cellulose and calcium phosphate may first be blended together, with the active then being added to the pre-blend and blending continued before adding the lubricant (followed by further blending, for a total of three blending steps). Alternatively, the active may be combined directly with the microcrystalline cellulose and calcium phosphate before any blending is performed, with the resulting mixture then being blended with the lubricant (i.e., only two blending steps are performed).

In simple terms, a process for preparing the particulate product of this invention may involve forming a well-mixed dry blend of microcrystalline cellulose and calcium phosphate, in which both materials are initially present and remain present as particulate solids. The relative amounts of the two components are adjusted in the blend to yield the specific weight ratio desired in the particulate product. Since the weight ratio of the two components in the particulate product corresponds closely to the relative amounts of the individual components to be blended together, this ratio adjustment is relatively straightforward.

The two components employed in forming the physical blend are microcrystalline cellulose and calcium phosphate, although one or more additional components may also be utilized if so desired. The source and nature of these components are not considered critical, except with respect to the particle size of the calcium phosphate.

The particle size of the microcrystalline cellulose used is ordinarily that which is encountered in conventional microcrystalline cellulose product. The particle size is desirably such that substantially all particles are less than No. 60 sieve (250 μm) in size. In one embodiment, the microcrystalline cellulose has a median particle size of from about 20 μm to about 250 μm.

Specific size requirements for fine particle sizes, if desired, can be met through screening off unwanted coarse material or through conventional wet or dry attrition procedures. These size reduction procedures are ordinarily not required with microcrystalline cellulose as is now commercially produced.

The calcium phosphate employed in the present invention may be any of the various calcium salts of phosphorus-containing acids (e.g., phosphoric acid) known in the art, particularly the pharmaceutical excipient art. Monobasic, dibasic, and tribasic calcium phosphates in anhydrous or hydrated form may be utilized. In situations where stability is critical, it may be preferred to use the anhydrous forms, as the hydrated forms may tend to lose their water of crystallization when heated. Anhydrous as well as hydrated dibasic calcium phosphates (e.g., dibasic calcium phosphate dihydrate and anhydrous dibasic calcium phosphate) are especially preferred. Dibasic calcium phosphate is sometimes also referred to as dicalcium phosphate, calcium monohydrogen phosphate, dicalcium orthophosphate, or secondary calcium phosphate. The use of U.S.P. or Ph.Eur. grades of calcium phosphates is also preferred. For example, certain of the dibasic calcium phosphates sold under the brand name Di-Cafos® by Budenheim are suitable for use in the present invention.

The median particle size of the calcium phosphate is desirably not more than 20 μm and in other embodiments of the invention is not more than 19, 18, 17, 16, 15, 14, 13, 12, 11, 10, 9, 8 or 7 μm. In one embodiment, the median particle size of the calcium phosphate is about 1 to about 10 μm, e.g., about 7 μm. The particle size of calcium phosphate may be varied as desired using any of the conventional techniques such as milling, grinding, attrition, and/or sieving. The median particle size can be measured by using, for example, a laser diffraction/scattering particle size distribution analyzer (e.g., Mastersizer 2000, manufactured by Malvern Instruments) and can be calculated as the midpoint of the particle size distribution, such that half the particles are larger in size than the D50 value and half the particles are smaller in size than the D50 value.

Moisture levels of not more than about 5 wt % H$_2$O are generally desired in the particulate product of the present invention.

The particulate product of the present invention is particularly useful as an excipient or binder in processes involving roller compaction, granulation, and/or tableting.

For example, the particulate product may be utilized in the following process:

1) The particulate product is blended with an API, a filler, and a disintegrant;
2) The blend from step 1 is further blended with a lubricant, if needed to reduce sticking on the compaction rolls;
3) The blend is compacted, using a roller compactor;
4) The ribbon obtained by roller compaction is granulated and/or milled;
5) The granulate obtained from step 4 is screened (to control and/or modify the particle size of the granulate, as needed or desired);
6) The screened granulate is recompacted to form tablets.

If needed to improve stability or to modify the disintegration time and dissolution rate or profile of the tablets, extragranular disintegrant and/or lubricant may be blended with the screened granulate prior to step 6. However, in at least some embodiments of the invention, the productivity (operating cost) of the dry granulation process is improved by avoiding such additional steps, which are generally considered necessary in traditional roller compaction processes which utilize binders and fillers other than the particulate product described herein.

Roller compaction (also known in the art as "roll compaction") is a dry compaction/granulation process for tablet formation, which is used when a tablet formulation does not have the flow characteristics or high enough bulk density necessary for tablet formation. A roller compactor uses pressure to compact and densify the tablet formulation and to bind powders into granules. Actives that have been processed by roller compaction include, for example, acetylsalicylic acid (aspirin), acetaminophen, amoxicillin, ibuprofen, penicillin, ranitidine, and streptomycin.

Figure 3:
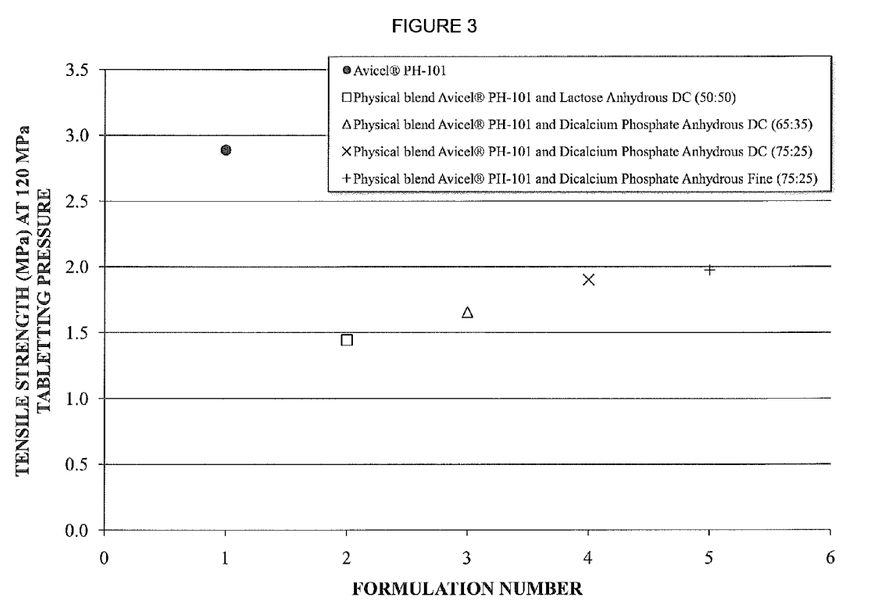
FIG. 3 is a graph comparing the compactibility of formulations containing Vitamin C, magnesium stearate and various excipients at a given tableting pressure.

The particulate product of the present invention is especially suitable for use in connection with a granulation process. Granulation is a process of size enlargement in which small particles are gathered together into larger aggregates in which the original particles can still be identified. Uniformly mixed powders (granulate formulations) are compressed between counter rotating rollers to form a ribbon of compacted material that is then milled into granules. Thus, the particulate product of the present invention may be used as an ingredient in a granulate formulation which is then converted into a granulate. A schematic representation of a roller compactor is shown in FIG. 3 of U.S. Patent Publication No. 2008/0213360, incorporated herein by reference in its entirety for all purposes. A roller compactor comprises a roller assembly, press frame, hydraulic pressure system, and a feed system. The feed system is located immediately before the rollers and determines the rate of flow of the granulate formulation to the rollers. The feed system may comprise one or more feed screws that force the granulate formulation between the compacting rollers. The granulate formulation is compacted as it passes through the two compacting rollers. The volume of the granulate formulation decreases as it passes through the region of maximum pressure, where it is formed into a solid compacted material known as a sheet or ribbon. Compaction pressure is provided by the hydraulic pressure system, which can be adjusted to produce the desired compaction pressure. The hydraulic pressure system acts on one of the rollers. As shown in FIG. 3 of U.S. Patent Publication No. 2008/0213360, the roller compaction process may be a continuous process of compacting, milling, screening, and recycling the too-large granules ("Overs") and too small granules ("Fines") back to the process. One advantage of the present invention is the reduction in the amount of Fines produced during such a process when the particulate product of the invention is employed as an excipient.

Various configurations for the rollers are well known in the art and are described, for example, in A. M. Falzone, Ph.D. Thesis, Purdue University, 1990 (U.M.I., Ann Arbor, Mich., Order Number 9313940). Roller compaction equipment is commercially available from the Fitzpatrick Company, Elmhurst Ill. USA as CHILSONATOR® roll compactors. This equipment is described in "Introduction to Roll Compaction and the Fitzpatrick CHILSONATOR," published by The Fitzpatrick Company Europe.

The particulate product of the present invention is also suitable for use as a component of a tablet, which may for example be prepared directly from a physical dry blend of the particulate product in combination with one or more additional ingredients such as an API or from a granulate prepared as previously described herein (also possibly in combination with one or more additional ingredients). Tabletting is well known to those skilled in the art of tablet formation. The tablet is formed by pressure being applied to the tablet formulation on a tablet press. A tablet press includes a lower punch which fits into a die from the bottom and an upper punch having a corresponding shape and dimension, which enters the die cavity from the top after the tablet formulation fills the die cavity. The tablet is formed by pressure applied to the tablet formulation in the die by the lower and upper punches. The ability of the tablet formulation to flow freely into the die is important in order to ensure that there is a uniform filling of the die with continuous flow of tablet formulation from hopper to die. A lubricant, such as magnesium stearate, may be added to facilitate ejection of the tablet from the die following compaction, and to avoid sticking to the punch faces. Tabletting is well described in pharmaceutics textbooks such as A GENNARO, Remington: The Science and Practice of Pharmacy, 20th Ed., Lippincott Williams & Wilkins, Baltimore, Md., 2000.

In one aspect, the present invention provides a solid dosage form such as a tablet comprising the particulate product of the invention, one or more actives, and, optionally, one or more one or more pharmaceutically acceptable excipients. Such tablets may be prepared from a tablet formulation by combining the active or actives with at least one excipient according to conventional pharmaceutical compounding techniques. To prepare a solid dosage form, or tablet, by direct compaction, the tablet formulation must have the necessary physical characteristics. Among other things, the tablet formulation must be free flowing, must be lubricated, and, importantly, must possess sufficient compactibility to ensure that the solid dosage form remains intact after compaction, and is robust enough for subsequent operations, such as handling, coating, and packaging. The particulate product of the present invention has been found to impart unexpectedly improved properties to tablet formulations, particularly with respect to compactibility and recompactibility.

The tablet may be formed by pressure being applied to the tablet formulation on a tablet press. A tablet press includes a lower punch that fits into a die from the bottom and an upper punch having a corresponding shape and dimension that enters the die cavity from the top after the tablet formulation fills the die cavity. The tablet is formed by pressure applied on the lower and upper punches. The ability of the tablet formulation to flow freely into the die is important in order to ensure that there is a uniform filling of the die and a continuous movement of the material from the source of the tablet formulation, e.g., a feeder hopper. The lubricity of the tablet formulation is crucial in the preparation of the solid dosage forms because the compressed material must be readily released from the punch faces. The tablet must also eject cleanly from the die following compression.

Because actives do not always have these properties, methods of tablet formulation have been developed in order to impart these desirable characteristics to the tablet formulation. Typically, the tablet formulation comprises one or more additives, or excipients, that impart the desired free flowing, lubrication, and binding properties to the tablet formulation.

The excipients for dry granulate formulations should have good recompactibility and dilution potential to allow compaction of the granules into a tablet. The excipients should not accelerate chemical and/or physical degradation of the active and should not interfere with its biological availability. The excipients should be physiologically inert and should not unintentionally interfere with the tablet disintegration or dissolution of the active. They should show low lubricant sensitivity and ensure acceptable active content uniformity. Typical excipients are selected from the group consisting of binders, disintegrants, glidants, fillers, diluents, colorants, flavorants, stabilizers, and lubricants. The choice of the excipients and the composition of the tablet formulation depend on the active, the amount of active in the formulation, the type of tablet, the desired characteristics for both the tablet formulation and the resulting tablet, and the manufacturing process used. These include prompt release, for which the drug dissolves in a very short time, immediate release and modified release, which include most of the orally administered tablets that are swallowed.

Pharmaceutically acceptable excipients are well known to those skilled in the art and are disclosed for example, in Staniforth, U.S. Pat. No. 6,936,277, and Lee, U.S. Pat. No. 6,936,628, each of which is incorporated herein by reference in its entirety for all purposes. Microcrystalline cellulose is added to improve the compactibility of the tablets. Excipients such as diluents, binders, glidants, and lubricants are added as processing aids to make the tableting operation more effective. Still other types of excipients enhance or retard the rate of disintegration of the tablet, improve the taste of the tablet (for example, sweetening agents), or impart a color or flavor to the tablets.

One or more lubricants may be added to a tablet formulation comprising the particulate product of the present invention to prevent the formulation from sticking to the punches during tablet manufacture. Suitable lubricants include, for example, fatty acids, fatty acid salts, and fatty acid esters such as magnesium stearate, calcium stearate, stearic acid, sodium stearyl fumarate, hydrogenated vegetable oil and the like. Lubricants may typically comprise about 0.1 wt % to about 3.0 wt % or about 0.5 wt % to about 1 wt % of the formulation. Antiadherents may be utilized to prevent sticking of the tablet formulation to the punch face and die wall. They are used in combination with magnesium stearate when sticking is a problem. Commonly used antiadherents are cornstarch and talc. Diluents, fillers, or bulking agents in addition to the particulate product of the present invention may be added in order to increase the bulk weight of the material to be tableted in order to make the tablet a practical size. This is often necessary where the dose of the active is relatively small. Suitable fillers for this purpose include, but are not limited to, lactose, dibasic calcium phosphate, calcium phosphate, powdered cellulose, dextrates, isomalt, calcium carbonate, magnesium carbonate, starch, pre-gelatinized starch, and mixtures thereof. Sugar alcohols such as sorbitol, mannitol and xylitol may also be used as fillers, especially in chewable tablet formulations. The most significant differences between sorbitol and mannitol are hygroscopicity and solubility. Sorbitol is hygroscopic above 65% relative humidity and mannitol is nonhygroscopic. The aqueous solubility of sorbitol is higher than mannitol.

One or more binders in addition to the particulate product of the present invention may be added to further modify the cohesive qualities of the powdered material(s). Suitable additional binders include starch, microcrystalline cellulose, and sugars such as sucrose, glucose, dextrose, and lactose. One or more stabilizers may be included in the tablet formulation to reduce the rate at which the active decomposes. Suitable stabilizers include antioxidants such as ascorbic acid. Additionally, one or more disintegrants may also be included in the tablet formulation to ensure that the tablet has an acceptable dissolution rate in an environment of use (such as the gastrointestinal tract). The disintegrant breaks up the tablets and the granules into particles of active and excipients. Superdisintegrants such as croscarmellose sodium, sodium starch glycolate, or crospovidone may also be employed.

One or more glidants may be used in the tablet formulation to improve flow. Because of the shape and size of the particles, glidants improve flow in low concentrations. They may be mixed in the final tablet formulation in dry form. Suitable glidants include, for example, alkali metal stearates, colloidal silicon dioxide (including materials sold under the brand names CAB-O-SIL®, SYLOID®, and AEROSIL®), and talc.

Desirable characteristics may be imparted to the tablet by colorants (i.e., dyes and pigments), natural or artificial sweeteners, and flavorants. Wetting agents, also called surface active agents or surfactants, may also be present. The tablet may also be coated.

Surfactants such as polysorbates, sodium lauryl sulphate, polyethylene glycol fatty acid esters, or polyethylene glycol ester salts may also be present in the formulation. To modify the release profile of the API, one or more matrix formers such as HPMC, carrageenan or alginate may optionally be included.

Tablets in accordance with the present invention may be any desired shape and size. For example, the size of round tablets may be about 50 mg to 500 mg and capsule-shaped tablets may be about 200 mg to 1200 mg in size. However, other formulations prepared in accordance with the invention may be suitably sized and shaped for other uses or locations, such as other body cavities, e.g., periodontal pockets, surgical wounds, and vaginally. For certain uses, such as chewable tablets, antacid tablets, vaginal tablets, and implants, the tablet may be larger.

The compositions are also suitable for use in enrobing processes to prepare solid dose forms. For example, solid dose forms may be prepared by lightly compacting a tablet formulation or granulate formulation in accordance with the present invention to form a powder compact and enrobing the powder compact with a film. The methods and apparatus for forming enrobed solid dose forms disclosed in WO 03/096963, WO 2005/030115, WO 2005/030116, WO 2005/030379, and WO 2006/032828, the disclosures of which are all incorporated herein by reference in their entirety for all purposes, may for example be adapted for use with solid dose forms prepared using the particulate products of the present invention.

The MCC/calcium phosphate-containing materials of the invention may be used as binders in solid dosage forms, such as tablets, that comprise one or more actives, and optionally, one or more other excipients. They are particularly useful as binders for formulations prepared by direct compression or processes involving compaction, granulation and recompaction. Although primarily useful in pharmaceutical and veterinary applications, they may be used in other areas, such as agriculture, food, cosmetics, and other industrial applications.

EXAMPLES

Glossary

Anhydrous EMCOMPRESS® dibasic calcium phosphate anhydrous, DC grade (JRS Pharma, Germany)
AVICEL® PH-101 50 µm microcrystalline cellulose (FMC, Philadelphia, Pa.)
Di-Cafos® C92-04 dibasic calcium phosphate anhydrous fine, 7 µm (Budenheim, Germany)
Di-Cafos® C92-05 dibasic calcium phosphate anhydrous fine, 7 µm (Budenheim, Germany)
Di-Cafos® C92-12 dibasic calcium phosphate anhydrous coarse, 80 µm (Budenheim, Germany)
EMCOMPRESS® Premium dibasic calcium phosphate dihydrate, DC grade ORS Pharma, Germany)
SuperTab® 21AN lactose anhydrous, DC grade (DMV Fonterra)
magnesium stearate Vegetable 2257 (Tyco Mallinckrodt, St Louis, Mo. USA)
Vitamin C ascorbic acid (crystalline) (Jiangsu Jiangshan Pharmaceutical Co., Ltd)

Unless otherwise stated, all percentages or proportions provided herein are stated as percentages or proportions based on weight.

Preparation and Methods

Roller-compacted ribbons and granulates were prepared and tested as follows:

Formulations containing 30 wt % Vitamin C were prepared by making a preblend of 6.95 kg of binder excipient(s) with 3 kg of Vitamin C as a model drug and blending for 10 minutes in a Pharmatech 50 Liter V Container rotating at 28 rotations per minute. Then 50 grams of magnesium stearate was added as a lubricant to the pre-blend and mixed for 2 minutes at 28 rpm. The blend, a total of 10 kg, was discharged. The same steps were repeated to produce a second blend of 10 kg using the same ingredients. The second blend was then discharged into the same bag as the first blend to obtain 20 kilograms. The formulation may be used for direct compression (e.g., to prepare tablets) or for forming granules (which may be recompacted to form tablets or other solid dosage forms).

The formulations were roller-compacted and then milled to form granulates at Fitzpatrick (The Fitzpatrick Company Europe, Entrepotstraat 8, B-9100 Sint-Niklaas, Belgium) on a pilot scale Chilsonator model IR-520/D6A. The roller compactor was equipped with knurled (grooved) rolls. The feeding auger or horizontal screw was rotating at 12 rpm, and the tamping auger or vertical screw was rotating at 200 rpm. These screw speeds were kept constant throughout the experiments. Compaction pressures were set at 20, 30 or 40 bars to compact the granulate formulations into a ribbon. The resulting gap or distance between the compaction rolls ranged between 1.2 and 1.8 millimeters depending on the compaction pressure applied on the powder/compact and on the granulate formulation being compacted. The mill used was of the type bar rotor rotating at 500 rpm and used in combination with a rasping screen having 1.0 millimeter openings. Approximately 2 kg of granulate were collected at each compaction pressure for each granulate formulation evaluated. Granulate from ribbons compacted at 30 bars was then compressed to form tablets on an ESH Compaction Simulator equipped with 13 millimeter round and flat punches. Compression force was applied only by the upper punch, while the lower punch was fixed during compression. The speed of the compaction simulator was set to obtain a mean compression (vertical) speed for the upper punch of 300 millimeters per second, which corresponds to a dwell time of approximately 6 milliseconds. Dwell time was defined as the time during which more than 90% of the maximum force is applied.

Example 1

The compactibility or tabletability of unlubricated calcium phosphates was evaluated on the compaction simulator. Due to the abrasive nature of these materials, punch tips and die walls were lubricated with a cotton swab dipped in a suspension of 5% magnesium stearate in acetone between each tablet to avoid obtaining high ejection forces and avoid damaging the toolings.

Emcompress® Premium dibasic calcium phosphate dihydrate for direct compression (median particle size about 130-150 µm), and Di-Cafos® C92-12, dibasic calcium phosphate anhydrous coarse (median particle size 80 µm), were compressed at high tableting speed, corresponding to a dwell time of approximately 6 milliseconds. Due to the low compactibility of Di-Cafos® C92-05 dibasic calcium phosphate anhydrous fine (median particle size 7 µm), compression speed was reduced for this material to obtain a dwell time of approximately 600 milliseconds.

Figure 1:
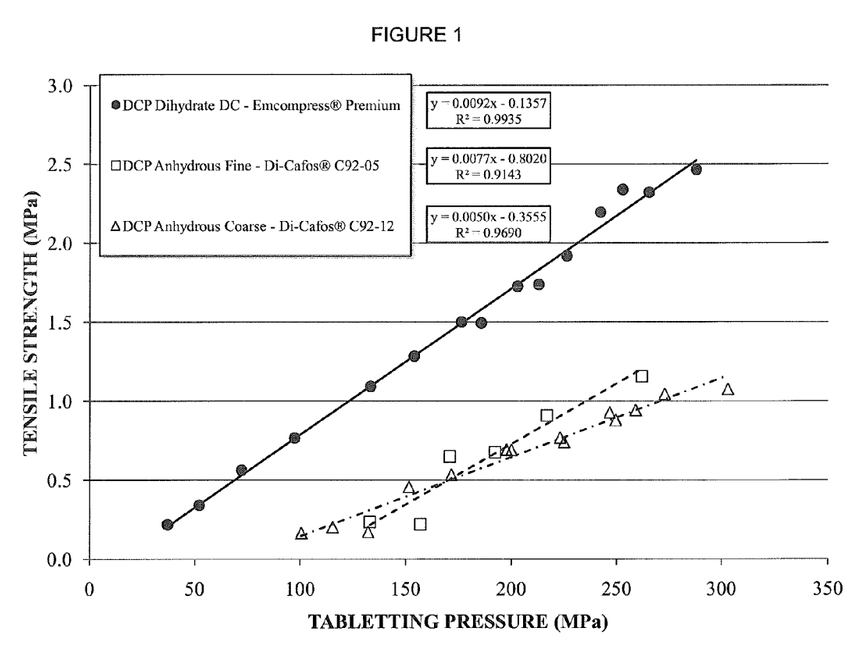
FIG. 1 is a graph comparing the compactibility of unlubricated or neat dibasic calcium phosphates.

The tabletability of these three calcium phosphates in direct compression is shown in FIG. 1, which plots tablet tensile strength versus tableting pressure. The direct compression grade of dibasic calcium phosphate is two times more compactible than the anhydrous grades. Indeed, at a tableting pressure of 250 MPa, Emcompress® Premium produces tablets having a tensile strength of about 2 MPa, whereas both anhydrous dibasic calcium phosphates generated tablets having tensile strengths of approximately 1 MPa.

Example 2

The compactibility or tabletability of several excipients was assessed in a Vitamin C formulation composed of 69.5% excipient(s), 30.0% Vitamin C, and 0.5% magnesium stearate (lubricant). Tabletting speed was set on the compaction simulator to obtain a dwell time of approximately 6 milliseconds.

Excipients were either Avicel® PH-101 or physical blends of Avicel® PH-101 with SuperTab 21AN (lactose anhydrous for direct compression) or Anhydrous Emcompress® (dibasic calcium phosphate anhydrous for direct compression) or Di-Cafos® C92-04 (dibasic calcium phosphate anhydrous fine).

Figure 2:
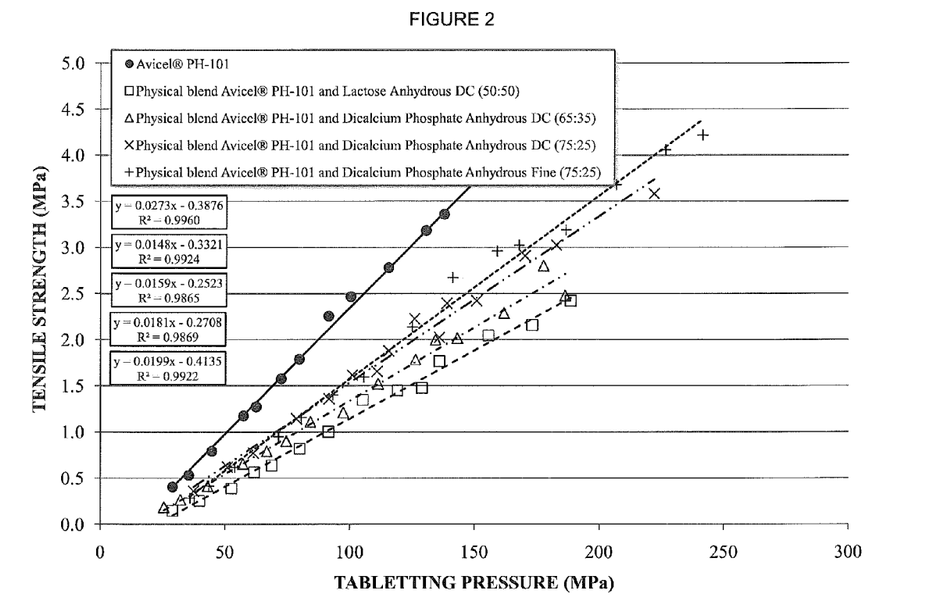
FIG. 2 is a graph comparing the compactibility of formulations containing Vitamin C, magnesium stearate and various excipients.

As indicated in FIG. 2, Avicel® PH-101, being more plastic than physical blends with lactose or dibasic calcium phosphates, provides the highest compactibility. It is therefore confirmed that microcrystalline cellulose is one of the best binders in direct compression as it provides the highest tensile strengths. The physical blend including dibasic calcium phosphate anhydrous fine provides similar compactibility compared to the physical blend including Anhydrous Emcompress®.

FIG. 3 plots tablet tensile strength at 120 MPa tableting pressure, based on the linear regression of FIG. 2. Both formulation including the physical blends of Avicel® PH-101 and 25% dibasic calcium phosphates have similar compactibility. This result is unexpected when considering the poor compactibility of neat dibasic calcium phosphates anhydrous fine, as illustrated in FIG. 1.

Example 3

The recompactibilities of Avicel® PH-101 and physical blends of Avicel® PH-101 and SuperTab® 21AN or dibasic calcium phosphates were assessed by tableting granules produced from ribbons formed by roller compaction (30 bars) of granulate formulations composed of 69.5% of Avicel® PH-101 or the blends, 30.0% Vitamin C, and 0.5% magnesium stearate.

Figure 4:
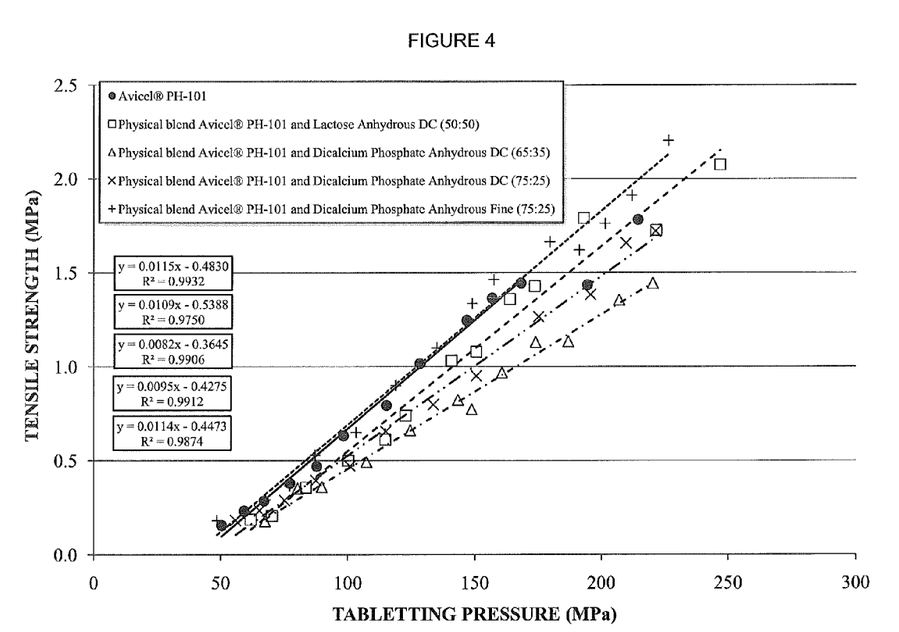
FIG. 4 is a graph comparing the recompactibility of formulations containing Vitamin C, magnesium stearate and various excipients.
Figure 5:
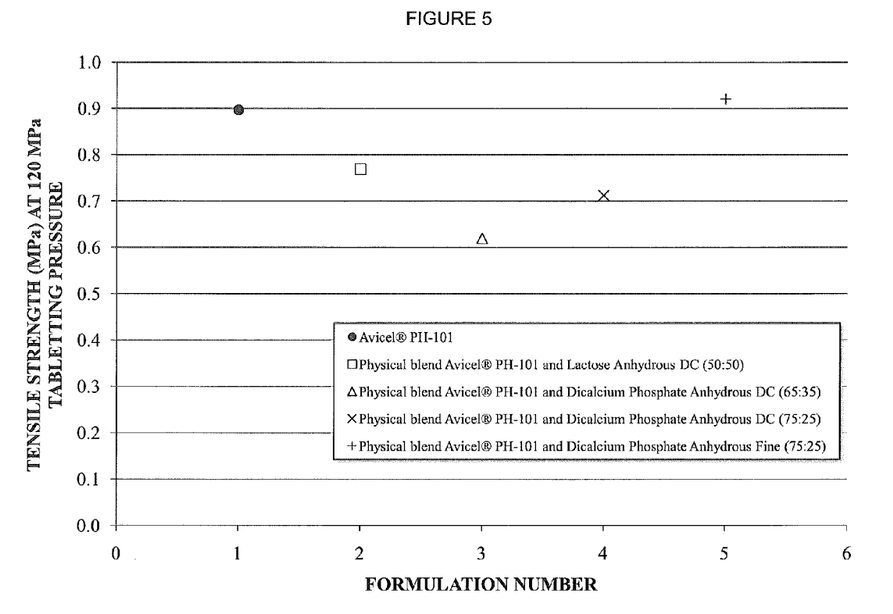
FIG. 5 is a graph comparing the recompactibility of formulations containing Vitamin C, magnesium stearate and various excipients at a given tableting pressure.

FIG. 4 plots tablet tensile strength versus tableting pressure and FIG. 5 plots tablet tensile strength at 120 MPa tableting pressure based on the linear regression of FIG. 4. The formulation containing the physical blend of Avicel® PH-101 and Di-Cafos® C92-04 was as recompactible as the formulation containing Avicel® PH-101 up to 170 MPa tableting pressure. Above this pressure the latter formulation showed first signs of defects, as indicated by the deviation from linearity in the tensile strength versus tableting pressure profile.

The formulation containing Di-Cafos® C92-04 was, however, significantly more recompactible than the equivalent formulation containing Anhydrous Emcompress®.

Example 4

The recompactibility and lubricant sparing ability of the physical blend of Avicel® PH-101 with Di-Cafos® C92-04 (dibasic calcium phosphate anhydrous fine) was assessed in comparison with Avicel® PH-101 and physical blends with lactose (SuperTab® 21AN) or a direct compression grade of dibasic calcium phosphate anhydrous (Anhydrous Emcompress®). Granules from ribbons formed by roller compaction (30 bars) of granulate formulation using of 69.5% of excipient(s), 30.0% Vitamin C, and 0.5% magnesium stearate were then lubricated with 1.0% extragranular magnesium stearate prior to being compressed on the compaction simulator.

Figure 6:
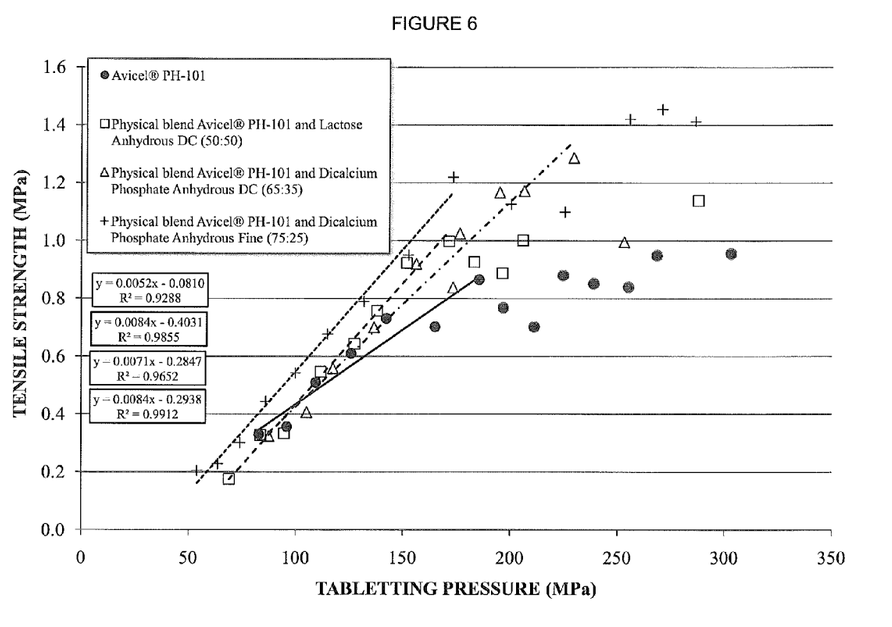
FIG. 6 is a graph comparing the recompactibility of formulations containing various excipients, Vitamin C, intragranular magnesium stearate and extragranular magnesium stearate.
Figure 7:
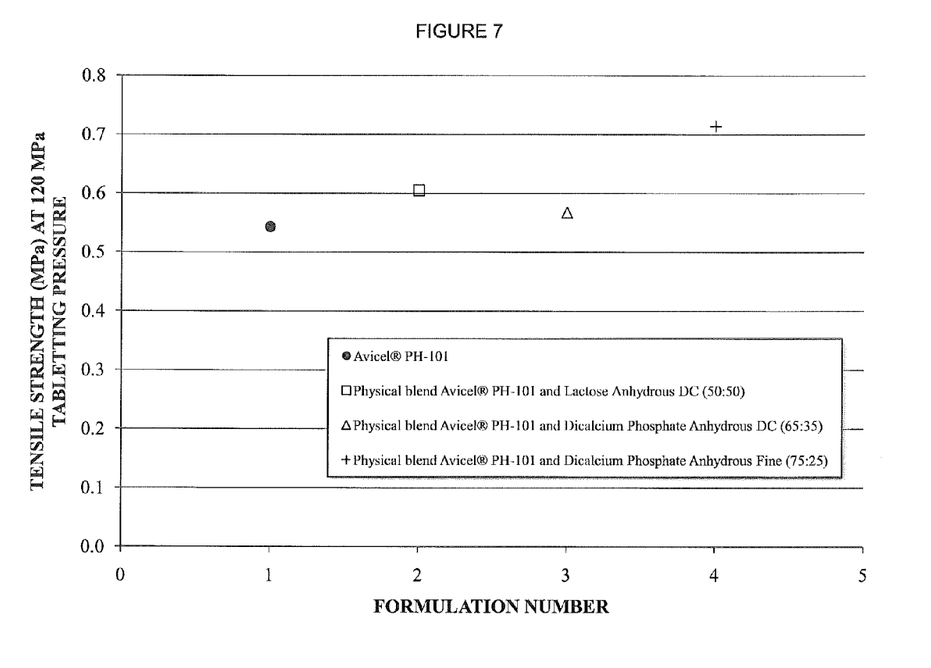
FIG. 7 is a graph comparing the recompactibility of formulations containing various excipients, Vitamin C, intragranular magnesium stearate and extragranular magnesium stearate at a given tableting pressure.

The physical blend of Avicel® PH-101 and 25% dibasic calcium phosphate anhydrous fine is more recompactible and less lubricant sensitive than Avicel® PH-101 or the blend with 35% of a direct compression grade of dibasic calcium phosphate anhydrous. This is shown in FIG. 6, tablet tensile strength versus tableting pressure, and FIG. 7, tablet tensile strength at 120 MPa tableting pressure based on the linear regression of FIG. 6.

Physical blends of microcrystalline cellulose with dibasic calcium phosphate anhydrous fine proved to be more suitable to dry granulation applications than microcrystalline cellulose on its own or blended with direct compression grades of dibasic calcium phosphate.

What is claimed is:

1. A composition useful as a pharmaceutical excipient in the preparation of tablets that are prepared by multiple compaction steps consisting of a physical blend of particles of at least one calcium phosphate and particles of microcrystalline cellulose, wherein the particles of at least one calcium phosphate have a median particle size as measured by laser diffraction of not greater than about 20 microns, and wherein tablets containing said composition have a higher tensile strength after recompaction at a tabletting pressure of 120 MPa than the same tablet consisting of a physical blend of microcrystalline cellulose and a calcium phosphate having a median particle size as measured by laser diffraction of greater than about 20 microns.

2. The composition of claim 1, wherein the particles of at least one calcium phosphate have a median particle size of not greater than about 15 microns.

3. The composition of claim 1, wherein the particles of at least one calcium phosphate have a median particle size of not greater than about 10 microns.

4. The composition of claim 1, wherein said at least one calcium phosphate includes dibasic calcium phosphate.

5. The composition of claim 1, wherein microcrystalline cellulose and the at least one calcium phosphate are present in a weight ratio of from about 85:15 to about 55:45 microcrystalline cellulose:calcium phosphate.

6. The composition of claim 1, wherein microcrystalline cellulose and the at least one calcium phosphate are present in a weight ratio of from about 80:20 to about 60:40 microcrystalline cellulose:calcium phosphate.

7. The composition of claim 1, wherein the calcium phosphate includes at least one of dibasic calcium phosphate dihydrate or anhydrous dibasic calcium phosphate.

8. The composition of claim 1, wherein the microcrystalline cellulose has a median particle size of about 20 µm to about 250 µm.

9. The composition of claim 1, wherein the composition is prepared by dry blending of calcium phosphate particles and microcrystalline cellulose particles.

10. A granulate or tablet formulation comprising the composition of claim 1 and at least one active.

11. The granulate or tablet formulation of claim 10, additionally comprising at least one lubricant.

12. The granulate or tablet formulation of claim 10, additionally comprising at least one disintegrant.

13. The composition of claim 1, wherein the microcrystalline cellulose and the at least one calcium phosphate are present in a weight ratio of from about 85:15 to about 75:25 microcrystalline cellulose:calcium phosphate.

14. A method comprising the steps of:
 a) applying pressure to a granulate formulation to form a compact, wherein the granulate formulation comprises the composition of claim 1 and at least one active; and
 b) milling the compact to form a granulate.

15. The method of claim 14, comprising an additional step of:
 c) recompacting the granulate to form a solid dosage form.

* * * * *